(12) United States Patent
Baughman et al.

(10) Patent No.: US 11,955,209 B2
(45) Date of Patent: Apr. 9, 2024

(54) COHORT SELECTION FOR AGILE PROCESSES

(71) Applicant: INTERNATIONAL BUSINESS MACHINES CORPORATION, Armonk, NY (US)

(72) Inventors: Aaron K. Baughman, Cary, NC (US); Alexandra Urman, New York, NY (US); Barry M. Graham, Silver Spring, MD (US); Christopher J. Dawson, Arlington, VA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 567 days.

(21) Appl. No.: 16/397,413

(22) Filed: Apr. 29, 2019

(65) Prior Publication Data

US 2020/0342961 A1  Oct. 29, 2020

(51) Int. Cl.
*G16H 10/20* (2018.01)
*G06F 16/28* (2019.01)

(52) U.S. Cl.
CPC ........... *G16H 10/20* (2018.01); *G06F 16/285* (2019.01)

(58) Field of Classification Search
CPC ....... G16H 10/20; G16H 20/10; G06F 16/285
USPC ...................................................... 705/2, 3
See application file for complete search history.

(56) References Cited

U.S. PATENT DOCUMENTS

| | | | |
|---|---|---|---|
| 6,904,434 B1 | 6/2005 | Wallach et al. | |
| 7,711,580 B1 | 5/2010 | Hudson | |
| 8,628,331 B1 | 1/2014 | Wright | |
| 2006/0282244 A1 | 12/2006 | Chotai et al. | |
| 2009/0292554 A1 | 11/2009 | Schultz | |
| 2010/0332258 A1* | 12/2010 | Dahlke | G16H 10/60 705/3 |
| 2012/0265544 A1 | 10/2012 | Hwang et al. | |
| 2018/0046780 A1 | 2/2018 | Graiver et al. | |

(Continued)

FOREIGN PATENT DOCUMENTS

| | | | | |
|---|---|---|---|---|
| CN | 109509512 A | * | 3/2019 | ............ G06F 40/18 |
| WO | 2010037838 | | 4/2010 | |

OTHER PUBLICATIONS

Patel et al., (2007), Matching Patient Records to Clinical Trials Using Ontologies (Year: 2007).*

(Continued)

*Primary Examiner* — Linh Giang Le
(74) *Attorney, Agent, or Firm* — Gavin Giraud; Andrew D. Wright; Calderon Safran & Cole, P.C.

(57) ABSTRACT

Methods and systems for cohort selection for agile processes are disclosed. A method includes: assigning, by a computing device, each of a plurality of entities to one of a plurality of groups; and for each of the plurality of groups: for each of the entities in the group, determining, by the computing device, information about the entity and encoding the determined information about the entity using a genetic algorithm; determining a ranking, by the computing device, of each of the entities in the group based on the encoded information about each of entity in the group; crossing over, by the computing device, portions of the encoded information of pairs of entities occupying adjacent positions in the ranking; and measuring, by the computing device, fitness of each of the entities in the group.

20 Claims, 7 Drawing Sheets

(56) References Cited

U.S. PATENT DOCUMENTS

| | | | | |
|---|---|---|---|---|
| 2019/0189286 | A1* | 6/2019 | Grady | G16H 10/20 |
| 2019/0347478 | A1* | 11/2019 | Sorci | G06K 9/627 |
| 2020/0012665 | A1* | 1/2020 | Das | G06F 16/285 |
| 2020/0251220 | A1* | 8/2020 | Chasko | G01C 21/206 |

OTHER PUBLICATIONS

Haupt et al, (2004), Practical Genetic Algorithms (Year: 2004).*

Konopka, Bogumil M et al. "Exploratory data analysis of a clinical study group: Development of a procedure for exploring multidimensional data." PloS one vol. 13,8 e0201950. Aug. 23, 2018 (Year: 2018).*

Wen Yu and ShengYi Jiang, "A Cluster-based Regrouping approach for Imbalanced data distributions," World Automation Congress 2012, 2012, pp. 121-124 (Year: 2012).*

Mell et al., "The NIST Definition of Cloud Computing", NIST, Special Publication 800-145, Sep. 2011, 7 pages.

Shivade et al., "Automatic Data Source Identification for Clinical Trial Eligibility Criteria Resolution." AMIA Annual Symposium Proceedings, 2016, p. 1149-1158, 10 pages.

Borlikova et al., "Development of a multi-model system to accommodate unknown misclassification costs in prediction of patient recruitment in multicentre clinical trials." In Proceedings of the Genetic and Evolutionary Computation Conference Companion (GECCO '17), 2017, p. 263-264, 2 pages.

Patel et al., "Matching Patient Records to Clinical Trials Using Ontologies." The Semantic Web. Lecture Notes in Computer Science, vol. 4825, 2007, 14 pages.

Qiu et al., "Statistical Genetic Interval-Valued Fuzzy Systems with Prediction in Clinical Trials," 2007 IEEE International Conference on Granular Computing (GRC 2007), 2007, p. 129-132, 4 pages.

Ni et al., "Increasing the Efficiency of Trial-Patient Matching: Automated Clinical Trial Eligibility Pre-Screening for Pediatric Oncology Patients." BMC Medical Informatics and Decision Making 15 (2015), 2018, 10 pages.

Chen et al., "'Sampling' as a Baseline Optimizer for Search-based Software Engineering", IEEE Computer Society, 2018, 16 pages.

Elgharbawy et al., "An agile verification framework for traffic sign classification algorithms in heavy vehicles", IEEE, 2016, Abstract, 3 pages.

Weskida et al., "Evolutionary algorithm for seed selection in social influence process", IEEE, 2016, Abstract, 3 pages.

Corporate Computer System Architects, "Transputer-based parallel processing products", ACM, ISBN:0-89791-278-0, 1988, Abstract, 2 pages.

Jun et al., "Automated routing protocol selection in mobile ad hoc networks", ACM, ISBN:1-59593-480-4, 2007, Abstract, 2 pages.

Garain et al., "A Bezier Curve Cohort Selection Strategy for Face Pair Matching", ACM, ISBN: 978-1-4503-6402-7, 2018, Abstract, 2 pages.

Jiang et al., "In-silico pre-clinical trials for implantable cardioverter defibrillators", IEEE, ISBN: 978-1-4577-0220-4, 2016, 4 pages.

Lin et al., "Evaluating the effectiveness of low level laser and cupping on low back pain by checking the plasma cortisol level", IEEE, 2014, Abstract, 4 pages.

Zhang et al., "Automatic patient search for breast cancer clinical trials using free-text medical reports", ACM, ISBN: 978-1-4503-0030-8, 2010, Abstract, 1 page.

Shankar et al., "Epoch: an ontological framework to support clinical trials management", ACM, ISBN: 1-59593-528-2, 2006, Abstract, 1 page.

* cited by examiner

COHORT SELECTION FOR AGILE PROCESSES

BACKGROUND

The present invention generally relates to computing devices and, more particularly, to methods and systems for cohort selection for agile processes.

An agile process such as a clinical study may employ steps that reflect an iterative, dynamic approach to optimizing the process and accomplishing an objective. Cohorts are groupings of entities such as people that are used in various processes such as clinical studies. Static criteria may be used to assign people and other entities to various cohorts.

SUMMARY

In a first aspect of the invention, there is a method that includes: assigning, by a computing device, each of a plurality of entities to one of a plurality of groups; and for each of the plurality of groups: for each of the entities in the group, determining, by the computing device, information about the entity and encoding the determined information about the entity using a genetic algorithm; determining a ranking, by the computing device, of each of the entities in the group based on the encoded information about each of entity in the group; crossing over, by the computing device, portions of the encoded information of pairs of entities occupying adjacent positions in the ranking; and measuring, by the computing device, fitness of each of the entities in the group.

In another aspect of the invention, there is a computer program product that includes a computer readable storage medium having program instructions embodied therewith. The program instructions are executable by a computing device to cause the computing device to: define decision variables for selecting a set of patients for a clinical trial; define restriction variables for the selecting the set of patients for the clinical trial; generate decision trees using training data from previous clinical trials; associate confidence values with the restriction variables; optimize an objective function for matching patients to the clinical trial; and assign the set of patients to the clinical trial based on the optimized objective function.

In another aspect of the invention, there is a system that includes: a hardware processor, a computer readable memory, and a computer readable storage medium associated with a computing device; program instructions to assign each of a plurality of entities to one of a plurality of groups; and program instructions to, for each of the plurality of groups: for each of the entities in the group, determine information about the entity and encoding the determined information about the entity using a genetic algorithm; determine a ranking of each of the entities in the group based on the encoded information about each of entity in the group; cross over portions of the encoded information of pairs of entities occupying adjacent positions in the ranking; and measure fitness of each of the entities in the group, wherein the program instructions are stored on the computer readable storage medium for execution by the hardware processor via the computer readable memory.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

Figure 1:
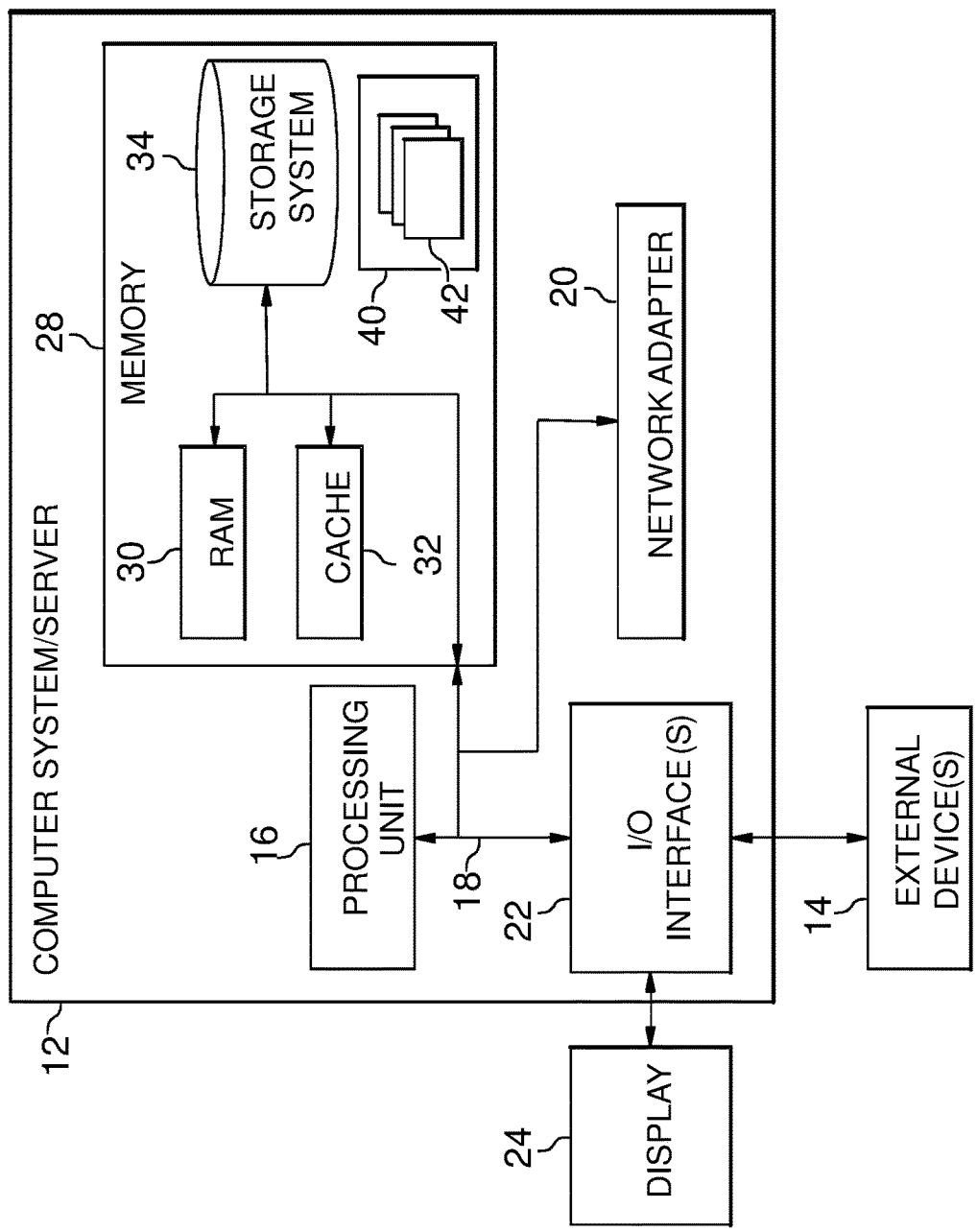
FIG. 1 depicts a cloud computing node according to an embodiment of the present invention.

The present invention generally relates to computing devices and, more particularly, to methods and systems for cohort selection for agile processes. In embodiments, in an agile process, cohorts (e.g., groupings of entities such as people) are dynamically created using an iterative algorithm. As described herein, aspects of the invention include a method and system for measuring persons or other entities within an agile process using feature extractors that identify environmental, epigenetic, physiological, and cognitive traits. Aspects of the invention also include a method and system for encoding the traits identified by the feature extractors into a DNA strand (e.g., a chromosome) using a genetic algorithm. Aspects of the invention also include a method and system for using the DNA strand for cohort evaluation and selection within the agile process.

In embodiments, cohort selection is mutated based on individual environmental, cognitive, and physiological effects. New cohorts may be generated by crossing paired individuals in a similar group. Additionally, individuals in a cohort may be encoded into a chromosome representation that includes environmental deep learning outputs, treatment/medicine features, and physiological/cognitive traits. In embodiments, sub-groups may be discovered to determine non-obvious relationships between environment, treatment/medicine, physiological, and cognitive state of individuals. New cohorts may be created with previous anomalous individuals by annealing them together through crossover and breeding of chromosomes. Additionally, in embodiments, the efficacy of treatments/medicines may be determined within created and shuffled groups to correlate agile cohorts to outcomes. Additionally, for groups with low treatment/medicine efficacy, the mutation rate may be increased to allow for increased independent variable exploration.

In embodiments, clinical trial patients are selected within agglomerative or decisive cohorts. In other embodiments, cohort evaluation and selection are used in other processes that need to become agile, with a particular emphasis on human groups.

Using conventional methods of assigning people and other entities to cohorts using static criteria (e.g., based on prior results) may result in people and other entities being assigned to non-optimal cohorts. Embodiments address these problems associated with conventional methods of assigning people and other entities to cohorts using static criteria. Accordingly, embodiments improve the functioning of a computer by providing methods and systems for iterative cohort selection for agile processes. (A process may be deemed "agile" if it employs steps that reflect an iterative, dynamic approach to optimization and accomplishing an objective.)

In particular, embodiments improve software by providing a method and system for dynamically creating cohorts using an iterative algorithm within an agile process. Embodiments also improve software by providing a method and system for measuring persons or other entities within an agile process using feature extractors that identify environmental, epigenetic, physiological, and cognitive traits. Embodiments also improve software by providing a method and system for encoding the traits identified by the feature extractors into a DNA strand using a genetic algorithm. Embodiments also improve software by providing a method and system for using the DNA strand for cohort evaluation and selection within the agile process. Additionally, implementations of the invention use techniques that are, by definition, rooted in computer technology (e.g., cloud computing, genetic algorithms, deep learning techniques, and convolutional neural networks).

Embodiments also improve software by providing for amorphous (agile) cohort group management instead of static cohort selection (e.g., based on prior results). In particular, embodiments discover subgroups that discern non-obvious relationships between the environment, a treatment/medicine, and a person's physiological and cognitive states. Additionally, embodiments create new cohorts to examine anomalous effects, dissolve cohorts having members that do not have close relationships, and automatically remove cohort participants over time (e.g., during the course of a multi-year clinical trial). Embodiments also improve software by providing for, in a clinical trial, determining the efficacy of a treatment/medicine with respect to the environment as well as cognitive and physiological feedback from a patient along with treatment/medicine properties (e.g., dosage). Additionally, embodiments provide for more flexible cohort selection and groupings without the need for any prior results (e.g., based on environmental or non-obvious variables).

To the extent the implementations collect, store, or employ personal information provided by individuals (e.g., participants in a clinical trial), it should be understood that such information shall be used in accordance with all applicable laws concerning protection of personal information. Additionally, the collection, storage, and use of such information, as well as, e.g., participation in any clinical trial, may be subject to consent of the individual to such activity, for example, through "opt-in" or "opt-out" processes as may be appropriate for the situation and type of information. Storage and use of personal information may be in an appropriately secure manner reflective of the type of information, for example, through various encryption and anonymization techniques for particularly sensitive information.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
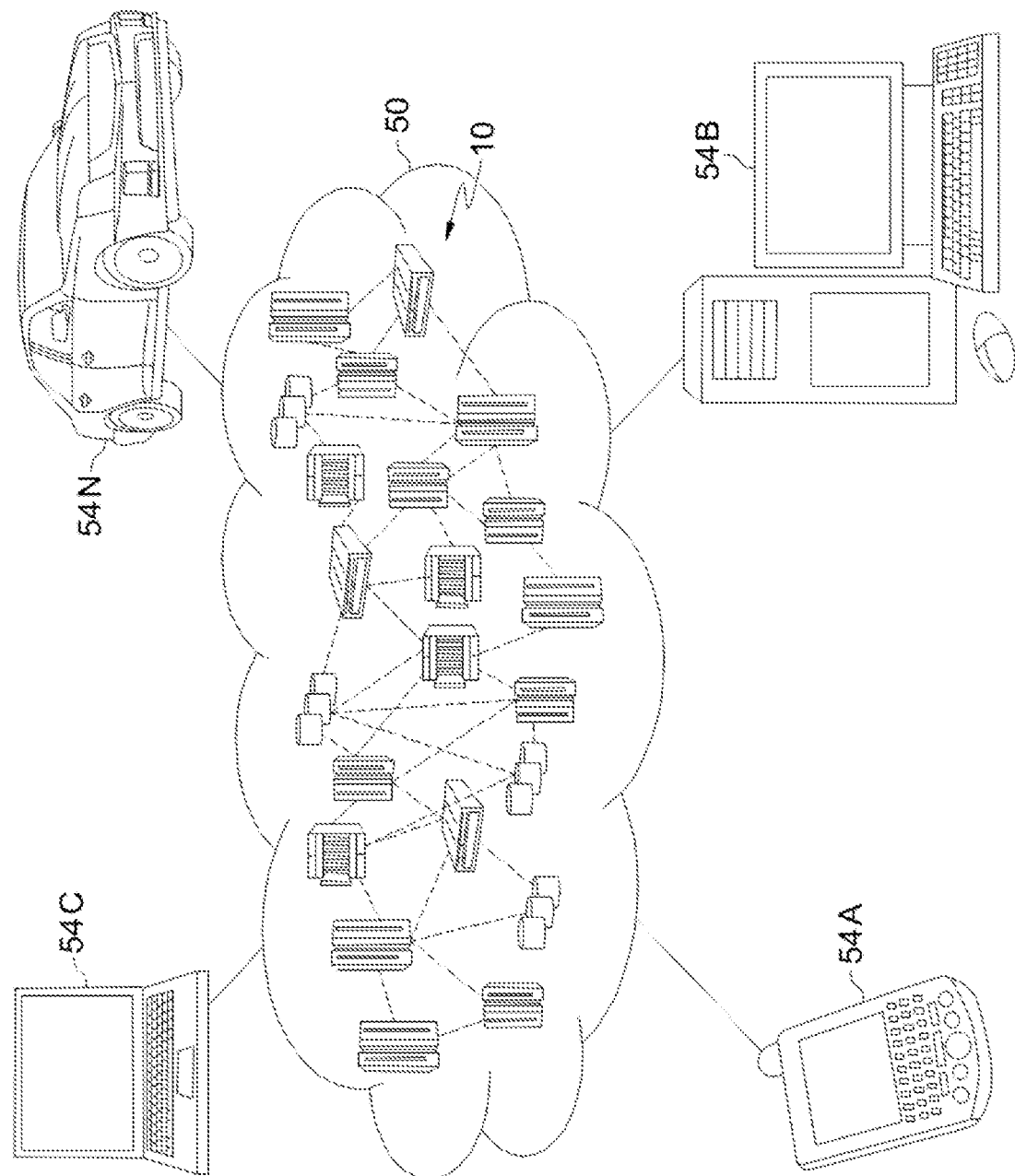
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
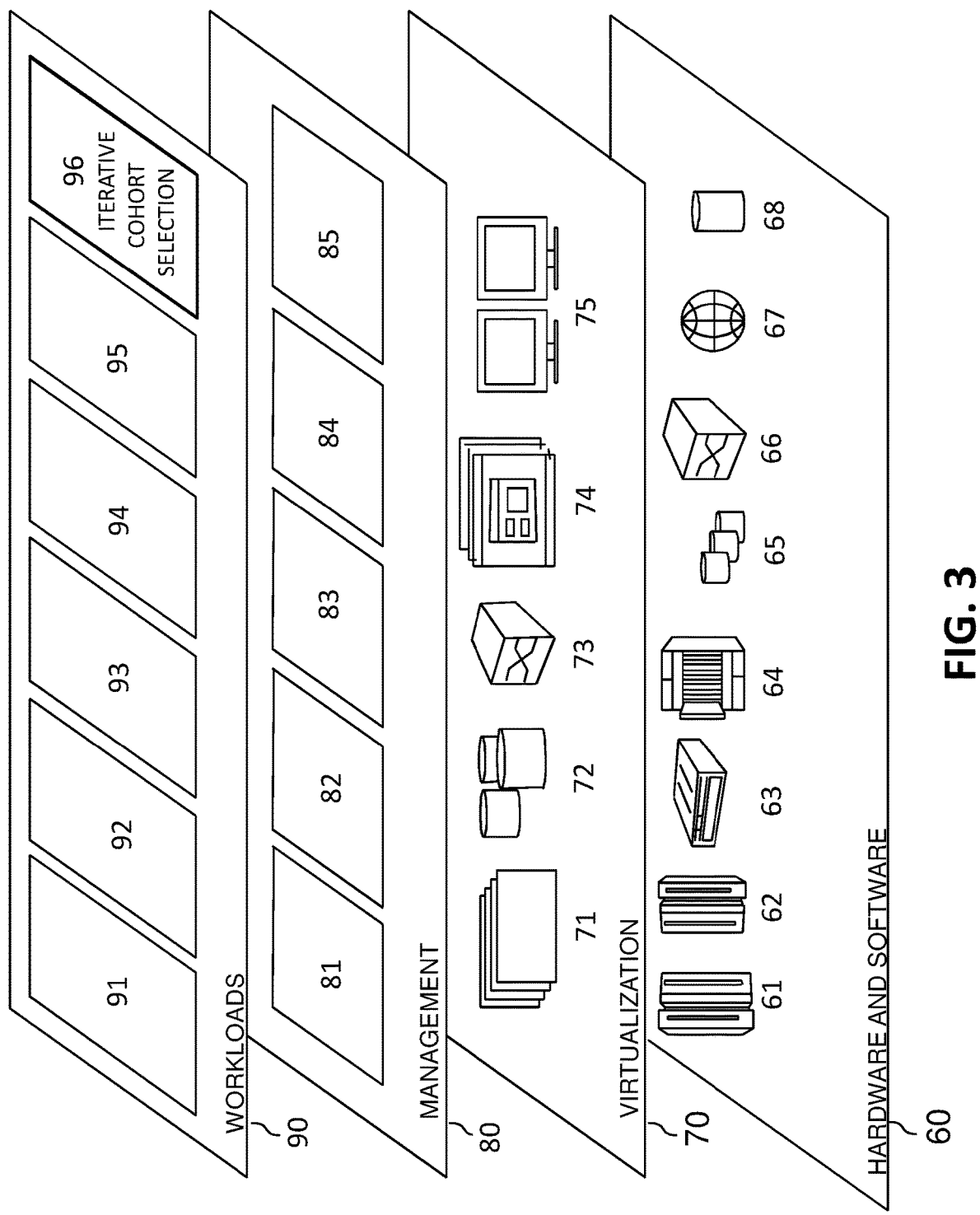
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and iterative cohort selection 96.

Referring back to FIG. 1, the program/utility 40 may include one or more program modules 42 that generally carry out the functions and/or methodologies of embodiments of the invention as described herein (e.g., such as the functionality provided by iterative cohort selection 96). Specifically, the program modules 42 may perform iterative cohort selection for agile processes. Other functionalities of the program modules 42 are described further herein such that the program modules 42 are not limited to the functions described above. Moreover, it is noted that some of the modules 42 can be implemented within the infrastructure shown in FIGS. 1-3. For example, the modules 42 may be representative of a cohort selection program module 410 as shown in FIG. 4.

Figure 4:
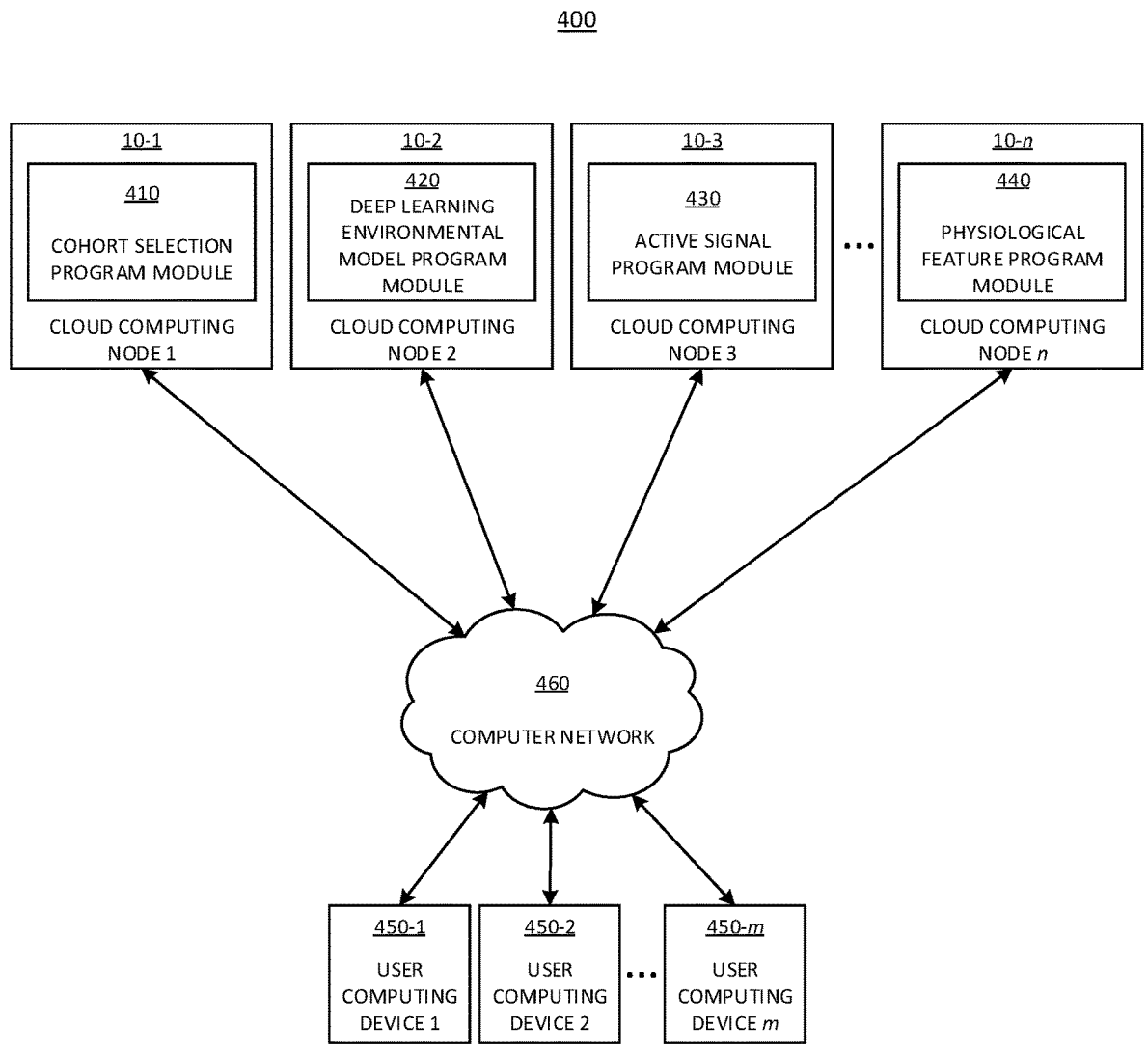
FIG. 4 depicts an illustrative environment in accordance with aspects of the invention.

FIG. 4 depicts an illustrative environment 400 in accordance with aspects of the invention. As shown, the environment 400 comprises a plurality of cloud computing nodes 10-1, 10-2, 10-3, . . . , 10-n and a plurality of user computing devices 450-1, 450-2, . . . , 450-m which are in communication via a computer network 460. In embodiments, the computer network 460 is any suitable network including any combination of a LAN, WAN, or the Internet. In embodiments, the plurality of cloud computing nodes 10-1, 10-2, 10-3, . . . , 10-n and the plurality of user computing devices 450-1, 450-2, . . . , 450-m are physically collocated, or, more typically, are situated in separate physical locations.

The quantity of devices and/or networks in the environment 400 is not limited to what is shown in FIG. 4. In practice, the environment 400 may include additional devices and/or networks; fewer devices and/or networks; different devices and/or networks; or differently arranged devices and/or networks than illustrated in FIG. 4. Also, in some implementations, one or more of the devices of the environment 400 may perform one or more functions described as being performed by another one or more of the devices of the environment 400.

In embodiments, each of the cloud computing nodes 10-1, 10-2, 10-3, . . . , 10-n may be implemented as hardware and/or software using components such as mainframes 61; RISC (Reduced Instruction Set Computer) architecture based servers 62; servers 63; blade servers 64; storage devices 65; networks and networking components 66; virtual servers 71; virtual storage 72; virtual networks 73, including virtual private networks; virtual applications and operating systems 74; and virtual clients 75 shown in FIG. 3. In embodiments, the cloud computing node 10-1 includes cohort selection program module 410 which provides for iterative cohort selection within an agile process, as described below. The cloud computing node 10-2 includes deep learning environmental model program module 420 which applies deep learning environmental models, as described below. The cloud computing node 10-3 includes active signal program module 430 which applies active signals, as described below. The cloud computing node 10-4 includes physiological feature program module 440 which extracts physiological features, as described below.

Still referring to FIG. 4, in embodiments, each of the user computing devices 450-1, 450-2, . . . , 450-m is a computer device comprising one or more elements of the computer system/server 12 (as shown in FIG. 1). In particular, each of the user computing devices 450-1, 450-2, . . . , 450-m is implemented as hardware and/or software using components such as mainframes; RISC (Reduced Instruction Set Computer) architecture based servers; servers; blade servers; storage devices; networks and networking components; virtual servers; virtual storage; virtual networks, including virtual private networks; virtual applications and operating systems; and virtual clients. In other embodiments, each of the user computing devices 450-1, 450-2, . . . , 450-m is a desktop computer, a laptop computer, a mobile device such as a cellular phone, tablet, personal digital assistant (PDA), an edge computing device, or other computing device.

Figure 5:
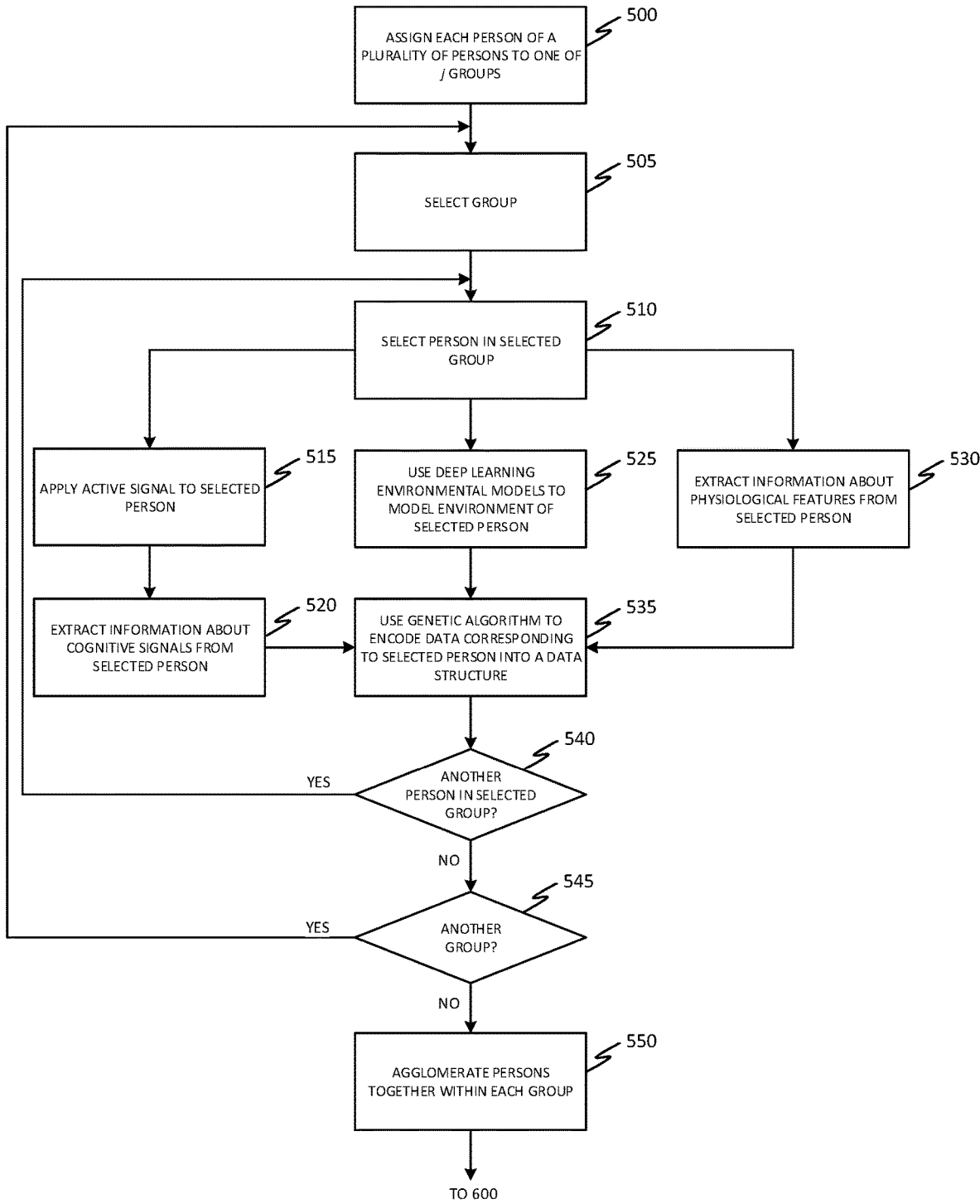
FIGS. 5, 6, and 7 depict flowcharts of exemplary methods performed in accordance with aspects of the invention.
Figure 6:
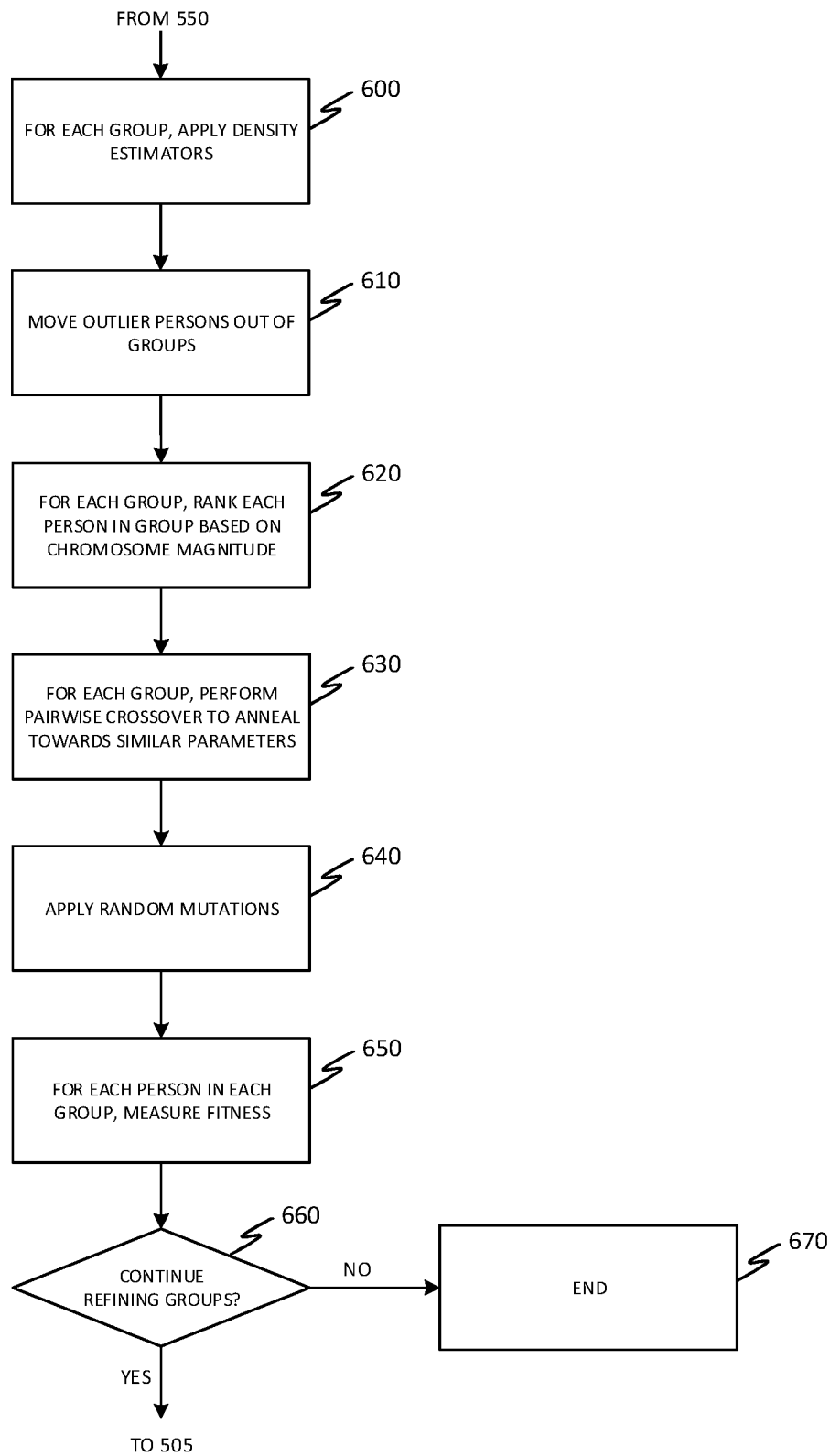

FIGS. 5 and 6 depict flowcharts of exemplary methods performed by the cohort selection program module 410 of the cloud computing node 10-1 in accordance with aspects of the invention. The steps of the methods are performed in the environment of FIG. 4 and are described with reference to the elements shown in FIG. 4.

At step 500, the cloud computing node 10-1 assigns each person (or entity) of a plurality of persons (or entities) to one of j groups (e.g., cohorts). In embodiments, in response to a request received from one of the user computing devices 450-1, 450-2, . . . , 450-m, the cohort selection program module 410 assigns each person (or entity) of a plurality of persons (or entities) participating in an agile process such as a clinical trial to one of the j groups or cohorts. The initial group assignment performed by the cohort selection program module 410 may be based on any criteria specified as part of the agile process (e.g., clinical trial). For example, the initial group assignment may be based on age, previous history with respect to reactions to a particular medicine, previous results, etc.

Still referring to FIG. 5, at step 505, the cloud computing node 10-1 selects a group. In embodiments, the cohort selection program module 410 selects a group that has not yet been selected (in the current iteration of the method of FIGS. 5 and 6) from the set of j groups into which the persons (or entities) were assigned at step 500. The cohort selection program module 410 may select the group on a sequential or random basis, or based on any other criteria that are predefined as part of the agile process (e.g., clinical trial).

Still referring to FIG. 5, at step 510, the cloud computing node 10-1 selects a person (or entity) in the selected group. In embodiments, the cohort selection program module 410 selects a person (or entity) that has not yet been selected (in the current iteration of the method of FIGS. 5 and 6) from the group selected at step 505. The cohort selection program module 410 may select the person (or entity) from the group on a sequential or random basis or based on any other criteria that are predefined as part of the agile process (e.g., clinical trial).

Still referring to FIG. 5, at step 515, the cloud computing node 10-1 applies an active signal to the selected person (or entity). In embodiments, the cohort selection program module 410 causes the active signal program module 430 of the cloud computing node 10-3 to apply the active signal to the person (or entity) selected at step 510. The active signal applied by the active signal program module 430 may be any kind of stimulus (e.g., auditory, visual, physical, etc.).

Still referring to FIG. 5, at step 520, the cloud computing node 10-1 extracts information about cognitive signals from the selected person (or entity). In embodiments, the cohort selection program module 410 causes the active signal program module 430 of the cloud computing node 10-3 to extract information about cognitive signals from the person selected at step 510 after and in response to the active signal being applied at step 515. In embodiments, the extracted cognitive signals are signals that indicate how the person is feeling after the active signal is applied at step 515.

For example, in an embodiment, the active signal program module 430 captures digital still images or digital video of the face of the person selected at step 510 and then analyzes the captured digital still images or digital video using a convolutional neural network to determine how the person is feeling after the active signal is applied at step 515. In other embodiments, the active signal program module 430 uses other automated or manual techniques to extract cognitive signals that indicate how the person is feeling after the active signal is applied at step 515.

Still referring to FIG. 5, at step 525, the cloud computing node 10-1 uses deep learning environmental models to model the environment of the selected person (or entity). In embodiments, the cohort selection program module 410 causes the deep learning environmental model program module 420 of the cloud computing node 10-2 to use the deep learning environmental models to model the environment of the person (or entity) selected at step 510. The deep learning environmental models applied by the deep learning environmental model program module 420 may be any kind of deep learning models that model the environment of the person selected at step 510. The models may output information about the selected person's environment (e.g., classifying various aspects of the person's environment).

Still referring to FIG. 5, at step 530, the cloud computing node 10-1 extracts information about physiological features from the selected person (or entity). In embodiments, the cohort selection program module 410 causes the physiological feature program module 440 of the cloud computing node 10-m to extract information about physiological features of the person (or entity) selected at step 510. The physiological features extracted by the physiological feature program module 440 may be any kind of features that indicate a response of the selected person from a physical standpoint (e.g., heart rate, blood pressure, etc.).

Still referring to FIG. 5, at step 535, the cloud computing node 10-1 uses a genetic algorithm to encode data corresponding to the selected person (or entity) into a data structure. In embodiments, the cohort selection program module 410 uses the genetic algorithm to encode data into a computer data structure that is termed a DNA strand (e.g., as a computer data structure that is termed a chromosome). In particular, the cohort selection program module 410 uses the genetic algorithm to encode, into a DNA strand (e.g., as a chromosome), data including the information about cognitive signals extracted at step 520 by the active signal program module 430 of the cloud computing node 10-3, the information about the selected person's environment output at step 525 by the deep learning environmental model program module 420 of the cloud computing node 10-2, and the information about physiological features extracted at step 530 by the physiological feature program module 440 of the cloud computing node 10-m. Additionally, in embodiments, the cohort selection program module 410 encodes, into the DNA strand (e.g., as the chromosome), information describing aspects of a therapy in a clinical trial (e.g., a medicine and a dosage) into the DNA strand for the selected person. In subsequent iterations of the method of FIGS. 5 and 6, at step 535, the cohort selection program module 410 uses the genetic algorithm to update the existing chromosome corresponding to the selected person to include new data received from steps 520, 525, and 530.

Still referring to FIG. 5, at step 540, the cloud computing node 10-1 determines whether or not there is another person (or entity) in the selected group. In embodiments, the cohort selection program module 410 determines whether or not there is another person (or entity) in the group selected at step 505 that has not yet been selected at step 510 in the current iteration of the method of FIGS. 5 and 6. If the cohort selection program module 410 determines that there is another person (or entity) in the group that has not yet been selected at step 510 in the current iteration, then the flow returns to step 510. On the other hand, if the cohort selection program module 410 determines that there is not another person (or entity) in the group that has not yet been selected at step 510 in the current iteration, then the flow proceeds to step 545.

Still referring to FIG. 5, at step 545, the cloud computing node 10-1 determines whether or not there is another group. In embodiments, the cohort selection program module 410 determines whether or not there is group that has not yet been selected at step 505 in the current iteration of the method of FIGS. 5 and 6. If the cohort selection program module 410 determines that there is another group that has not yet been selected at step 505 in the current iteration, then the flow returns to step 505. On the other hand, if the cohort selection program module 410 determines that there is not another group that has not yet been selected at step 505 in the current iteration, then the flow proceeds to step 550.

Still referring to FIG. 5, at step 550, the cloud computing node 10-1 agglomerates persons (or entities) together within each group. In embodiments, for each of the j groups, the cohort selection program module 410 compares the chromosomes encoded at step 535 for all of the persons (or entities) in the group and identifies clusters of chromosomes having similar information encoded therein. The cohort selection program module 410 agglomerates together persons (or entities) represented by the clustered chromosomes within each group (i.e., persons who are determined to be similar based on the information encoded in their chromosomes). The flow then proceeds to step 600 (of FIG. 6).

Referring to FIG. 6, at step 600, the cloud computing node 10-1, for each group, applies density estimators. In embodiments, for each of the j groups, the cohort selection program module 410 applies a gaussian mixture model to all of the chromosomes in the group to identify outlier chromosomes. In particular, in an embodiment, the cohort selection program module 410 identifies an epicenter of one or more chromosome clusters in the group and determines that any chromosomes that are more than a predetermined number of standard deviations (e.g., more than 2) away from an epicenter of one of the chromosome clusters are outlier chromosomes. In this way, persons (or entities) corresponding to the outlier chromosomes are determined to be outlier persons (or entities).

Still referring to FIG. 6, at step 610, the cloud computing node 10-1 moves the outlier persons (or entities) out of the groups. In embodiments, for each of the j groups, the cohort selection program module 410 moves each of the outlier persons (i.e., persons represented by the chromosomes determined to be outlier chromosomes at step 600) out of the group.

Still referring to step 610, in embodiments, each person (or entity) that is moved out of a group is moved by the cohort selection program module 410 into another group of the j groups in which the person's (or entity's) chromosome is positioned closest to (and within the predetermined number of standard deviations of) an epicenter of one of the chromosome clusters from step 600. If the person's (or entity's) chromosome is not within the predetermined number of standard deviations of an epicenter of one of the chromosome clusters from step 600 in any of the j groups, then the cohort selection program module 410 creates a new group and moves the person (or entity) into that new group. (Note that j is then incremented by one to reflect the increased number of groups.)

Still referring to FIG. 6, at step 620, the cloud computing node 10-1, for each group, ranks each person (or entity) in the group based on chromosome magnitude. In embodiments, for each of the j groups, the cohort selection program module 410 ranks each person (or entity) based on the magnitude of the chromosome corresponding to the person (or entity).

Still referring to step 620, in embodiments, the cohort selection program module 410 takes the sum of the square of all of the values encoded into a person's (or entity's) chromosome, divided by the number of values encoded into the chromosome, and performs the ranking based on the result. In the second and subsequent iterations of the method of FIGS. 5 and 6, the cohort selection program module 410 also uses the fitness value calculated at step 650 (described below) in the ranking (e.g., the fitness value is averaged with the magnitude of the chromosome). In embodiments, the ranking indicates how each person in the group responds to a therapy in a clinical trial. Comparatively higher signal values (from steps 520, 525, and 530 of FIG. 5) encoded into the chromosome (at step 535 of FIG. 5) indicate a comparatively greater response and therefore result in a comparatively higher ranking at step 620.

Still referring to FIG. 6, at step 630, the cloud computing node 10-1, for each group, performs pairwise crossover to anneal towards similar parameters. In embodiments, for each of the j groups, the cohort selection program module 410 performs pairwise crossover by selecting chromosomes associated with persons (or entities) that are adjacent in the ranking from step 620 (e.g., chromosomes associated with the first and second ranked persons, chromosomes associated with the third and fourth ranked persons, etc.) and crossing over portions of the DNA strand in the chromosomes that describe aspects of a therapy in the clinical trial. For example, medicine dosages may be swapped between the two chromosomes in each pair.

Still referring to FIG. 6, at step 640, the cloud computing node 10-1 applies random mutations. In embodiments, for each of the j groups, the cohort selection program module 410 applies a random mutation to a predetermined percentage of the chromosomes in the group. For a particular chromosome, the random mutation adjusts portions of the DNA strand in the chromosome that describe aspects of a therapy in the clinical trial, within a predetermined allowable amount. For example, the cohort selection program module 410 may select 5% of the chromosomes in each group, and for each selected chromosome, may adjust a medicine dosage randomly within a predetermined minimum/maximum threshold (e.g., +/−10% of the current value). Selecting higher percentages of chromosomes to apply a random mutation may aid in exploration of a larger space, while selecting lower percentages of chromosomes to apply a random mutation may move the clinical trial towards convergence on a solution (though possibly a non-optimal solution).

Still referring to FIG. 6, at step 650, the cloud computing node 10-1, for each person (or entity) in each group, measures fitness. In embodiments, for each of the j groups, for each person in the group, the cohort selection program module 410 measures the fitness of the person using the data encoded in the chromosome corresponding to the person.

Still referring to step 650, the cohort selection program module 410 may measure fitness by receiving information indicating how well a person represented by the chromosome is responding to a therapy in the clinical trial (e.g., medicine efficacy). This information may be in the form of survey data (e.g., from a survey asking a person how they are doing and/or how they feel they are responding to treatment), physician data (e.g., an evaluation from a physician of how a person is responding to treatment), physiological data (e.g., blood pressure, blood glucose levels, electrocardiogram data, etc.). The cohort selection program module 410 may receive the information indicating how well a person represented by the chromosome is responding to a therapy in the clinical trial directly from a monitoring device (e.g., blood pressure monitor, glucose monitor, electrocardiograph), or via one of the user computing devices 450-1, 450-2, . . . , 450-m. In embodiments, after receiving the information indicating how well a person represented by the chromosome is responding to a therapy in the clinical trial directly from a monitoring device, the cohort selection program module 410 uses a fitness function that is predefined by an administrator (e.g., an administrator of the clinical trial) to determine a fitness value for the person corresponding to the chromosome. A comparatively higher fitness value indicates that a person corresponding to the chromosome is responding comparatively better to a therapy in the clinical trial than a person having a comparatively lower fitness value.

Still referring to FIG. 6, at step 660, the cloud computing node 10-1 determines whether or not to continue refining the groups. In embodiments, the cohort selection program module 410 determines whether or not to continue refining the groups. In an embodiment, the groups may continue to be refined throughout the course of a clinical trial, to optimize the groupings over the course of time as persons have had further therapy in the clinical trial. If the cohort selection program module 410 determines that the groups should continue to be refined (e.g., if the clinical trial is ongoing), then the flow returns to step 505 (of FIG. 5), and a new iteration of the method of FIGS. 5 and 6 begins. On the other hand, if the cohort selection program module 410 determines that the groups should not continue to be refined (e.g., if the clinical trial has concluded), then the flow proceeds to step 670, and the method ends.

In an example, the method described above with respect to FIGS. 5 and 6 may be used for mutation and crossing over in clinical trials. In particular, models are applied and features are extracted as described above with respect to steps 511, 520, 525, and 530 for persons that are available to participate in the clinical trial, and the information is encoded into a DNA strand as described above with respect to step 535. Additionally, a set of variables is encoded into the DNA strand at step 535. The variables encoded into the DNA strand, for example, may include a dosage amounts of medications, medical equipment or procedures such as transcranial magnetic stimulation (TMS) or repetitive transcranial magnetic stimulation (rTMS), as well as parameters for equipment. The groups are then stratified into clusters as described with respect to step 600, based on the information from the models and extracted features that are encoded into the DNA strands. At step 630, variables that are related to a current set of criteria in the clinical trial are crossed over to generate new criteria to explore cause and effect. The crossover rate is comparatively highest for groups with comparatively higher amounts of variables. Additionally, the random mutations at step 640 may be applied at comparatively higher rates for groups with comparatively higher amounts of variables. The crossover at step 630 and the random mutation at step 640 produce new variables and combinations for each group. Additionally, the new cohort selections and groups (e.g., as described with respect to step 610) are presented to a user of one of the user computing devices 450-1, 450-2, . . . , 450-*m* and updated on the cloud in real time.

Figure 7:
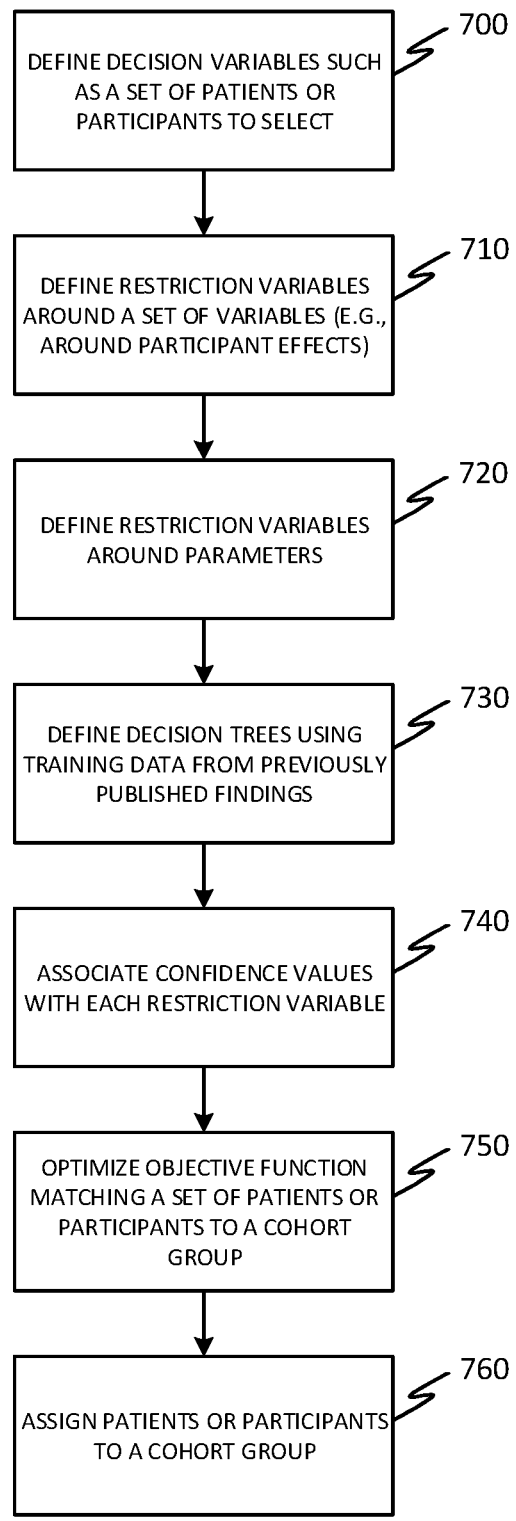

FIG. 7 depicts a flowchart of another exemplary method performed by the cohort selection program module 410 of the cloud computing node 10-1 in accordance with aspects of the invention. The steps of the method are performed in the environment of FIG. 4 and are described with reference to the elements shown in FIG. 4.

At step 700, the cloud computing node 10-1 defines decision variables such as a set of patients or participants to select. In embodiments, the cohort selection program module 410 defines the decision variables such as the set of patients or participants to select.

Still referring to FIG. 7, at step 710, the cloud computing node 10-1 defines restriction variables around a set of variables (e.g., around participant effects). In embodiments, the cohort selection program module 410 defines the restriction variables around the set of variables (e.g., around participant effects).

Still referring to FIG. 7, at step 720, the cloud computing node 10-1 defines restriction variables around parameters. In embodiments, the cohort selection program module 410 defines the restriction variables around demographics (e.g., location, gender, ethnicity, age, etc.).

Still referring to FIG. 7, at step 730, the cloud computing node 10-1 defines decision trees using training data from previously published findings. In embodiments, the cohort selection program module 410 defines the decision trees using the training data from previously published findings (e.g., previously finished trials that are most like the emerged trial).

Still referring to FIG. 7, at step 740, the cloud computing node 10-1 associates confidence values with each restriction variable. In embodiments, the cohort selection program module 410 associates the confidence values with each restriction variable.

Still referring to FIG. 7, at step 750, the cloud computing node 10-1 optimizes an objective function matching a set of patients or participants to a cohort group. In embodiments, the cohort selection program module 410 optimizes the objective function matching a set of patients or participants to a cohort group.

Still referring to FIG. 7, at step 760, the cloud computing node 10-1 assigns patients or participants to a cohort group. In embodiments, the cohort selection program module 410 assigns the patients or participants to a cohort group. In embodiments, patients are assigned to emerged trials in real time.

In another embodiment, a system and method are provided for automatically updating clinical trial enrollment in real-time for multiple institutions for competitive enrollment clinical trials on the cloud. Additionally, cognitive technology alerts users when trials are likely to be available as well as when enrollment is low and suggest best dates for the patient to come in to have their best chance of getting on the trial (i.e., no other physician consenting a patient at another institution first) based on algorithms and natural language processing (NLP) capabilities that the cognitive technology uses to assess common patterns of physicians in the study.

In particular, a system and method are provided for quickly updating clinical trial enrollment numbers in real-time on the cloud so that multiple institutions or sites can view it concurrently and right when it happens. This avoids multiple patients signing consent for competitive enrollment clinical trials at the same time and it avoids giving false hope to patients when clinical trials are already closed. It gives doctors and research study staff an idea of how many spots are left on clinical trials and therefore they can plan their patient schedules accordingly and have the patient(s) that they are considering for a trial come in earlier if need be. It also eliminates e-mail communication between a sponsor and a site about enrollment numbers and therefore saves time and effort. Furthermore, to ensure that a clinician does not miss getting a patient on a clinical trial due to no enrollment spots left, cognitive and NLP capabilities are used to review enrollment logs located on the cloud of multi-site competitive enrollment trials and suggest dates and times that may work best for the patient to come in. Accordingly, embodiments improve patient enrollment numbers in competitive clinical trials, reduce time and effort required for pharmaceutical companies to obtain enrollment data, reduce time required for clinical trial coordinators to relay information, and reduce instances of patients receiving inaccurate information about clinical trial enrollment availability.

In other embodiments, a system and method is provided for mutating clinical trials based on groups tactile participant effects, breeding new clinical trials by crossing competitive trials, reducing tactile participant effects by determining psychological side effects factors in real time, reducing tactile participant effects by determining physiological side effects factors in real time, and reducing tactile participant effects by determining environmental side effects factors in real time.

In other embodiments, a system and method are provided for integrating with cognitive trial matching software which searches for clinical trials for which a patient may be eligible. A cloud based solution is provided that predicts based on analytics when a trial will be available and updates in real time when a patient is put on a clinical trial. Further, embodiments indicate when enrollment is low for a particular clinical trial and advise when a patient should be seen (so that another doctor has not already consented another patient) based on NLP and algorithms modeling those doctors' typical consenting practices.

In other embodiments, a system and method are provided for mutation and crossing over clinical trials. First, a clinical trial is encoded into a DNA strand. The variables such as dosage amounts of medications, medical equipment such as TMS and rTMS, as well as parameters for equipment are encoded onto the strand. Second, participant effect models are applied to participants that are available. Third, groups are stratified into clusters based on the results of the second step. Fourth, a highest mutation rate is applied to the groups with high tactile participant effects. Fifth, clinical trials that are related to the current trial are crossed over to generate new trials to explore cause and effect. Sixth, a highest crossover rate is applied to the groups with high tactile participant effects. Seventh, mutations and crossover operators produce new trials for each group. Eighth, the new trial and group is presented to the physicians and updated on the cloud in real time.

In other embodiments, a system and method are provided for patient selection within a pool of an emerged trial and group. First, decision variables are defined such as a set of patients to select. Second, restriction variables are defined around participant effects. Third, restriction variables are defined around location, gender, ethnicity, age. Fourth, decision trees use training data from previously finished trials that are most like the emerged trial. Fifth, confidence values are associated with each restriction variable. Sixth, the objective function of matching a set of patients to emerged trials is optimized. Seventh, patients are assigned to emerged trials in real time In embodiments, a service provider could offer to perform the processes described herein. In this case, the service provider can create, maintain, deploy, support, etc., the computer infrastructure that performs the process steps of the invention for one or more customers. These customers may be, for example, any business that uses cloud computing technology. In return, the service provider can receive payment from the customer(s) under a subscription and/or fee agreement and/or the service provider can receive payment from the sale of advertising content to one or more third parties.

In still additional embodiments, the invention provides a computer-implemented method, via a network. In this case, a computer infrastructure, such as computer system/server 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system/server 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:

assigning, by a computing device, each of a plurality of entities to one of a plurality of treatment groups, resulting in groups of entities, wherein the plurality of entities are participants in a clinical trial; and for each of the plurality of treatment groups:

for each of the entities in a group of the plurality of treatment groups, determining, by the computing device, environmental features of an entity in real time during the clinical trial utilizing a deep learning environmental model outputting classified aspects of the entity's environment;

for each of the entities in the group of the plurality of treatment groups, obtaining, by the computing device, physiological measurements of the entity directly from a monitoring device of the entity during the clinical trial;

for each of the entities in the group of the plurality of treatment groups, determining, by the computing device, an indication of how the entity is feeling in response to an active signal applied to the entity by analyzing digital images of the entity using a convoluted neural network;

for each of the entities in the group of the plurality of treatment groups, determining, by the computing device, variables associated with the clinical trial;

for each of the entities in the group of the plurality of treatment groups, encoding, by the computing device, determined information about the entity during the clinical trial including the classified aspects of the entity's environment, the physiological measurements of the entity, the indication of how the entity is feeling, and the determined variables associated with the clinical trial, into a computer data structure as chromosomes using a genetic algorithm;

for each of the entities in the group of the plurality of treatment groups, iteratively updating, by the computing device, the chromosomes based on new determined information about the entity obtained during the clinical trial;

automatically determining, by the computing device, one or more outlier chromosomes of the chromosomes;

automatically removing, by the computing device, one or more outlier entities in the group of the plurality of treatment groups based on the determined outlier chromosomes;

determining a ranking, by the computing device, of each of the entities in the group of the plurality of treatment groups based on a magnitude of values of the chromosomes corresponding to each entity in the group, wherein the ranking indicates how each entity in the group responds to a therapy in the clinical trial;

for each group in the plurality of treatment groups, crossing over, by the computing device, portions of the encoded information of pairs of entities occupying adjacent positions in the ranking that describe aspects of the clinical trial to create new trial variables regarding aspects of the clinical trial, including dosage amounts of a medication;

sending, by the computing device, the new trial variables to a user; and measuring, by the computing device, fitness of each of the entities in the group of the plurality of treatment groups based on their respective chromosomes.

2. The method according to claim 1, further comprising, for each of the plurality of treatment groups, agglomerating, by the computing device, the entities in the group based on a determined level of similarity.

3. The method according to claim 2, further comprising, for each of the plurality of treatment groups, applying density estimators, by the computing device, to the entities in the group.

4. The method according to claim 3, further comprising, for each of the plurality of treatment groups, identifying, by the computing device, the one or more outlier chromosomes by applying a gaussian mixture model to all of the chromosomes in the group.

5. The method according to claim 4, wherein the removing the one or more outlier entities out of the group comprises moving the one or more outlier entities to another group of the plurality of treatment groups.

6. The method according to claim 4, wherein the removing the one or more outlier entities out of the group comprises moving the one or more outlier entities to a newly created group.

7. The method according to claim 1, wherein the encoded information includes information on the therapy in the clinical trial.

8. The method according to claim 7, further comprising:
selecting, by the computing device, an entity from the entities in one of the plurality of treatment groups of entities; and
extracting, by the computing device, information about cognitive signals from digital data of the selected entity, wherein the information about the entity includes the information about the cognitive signals, wherein the crossing over the portions of the encoded information comprises crossing over information describing aspects of the therapy in the clinical trial.

9. The method according to claim 8, further comprising applying an active signal to the selected entity, wherein:
the active signal comprises a stimulus; and
the cognitive signals indicate how the selected entity feels in response to the active signal.

10. The method according to claim 9, wherein the extracting information about cognitive signals from the selected entity comprises:
capturing digital still images or digital video of the selected entity, wherein the digital images comprise the digital still images or the digital video; and
the extracting the information about cognitive signals includes determining how the selected entity feels in response to the active signal by analyzing the digital still images or the digital video of the selected entity.

11. The method according to claim 10, wherein the analyzing the digital still images or digital video of the selected entity comprises analyzing the digital still images.

12. The method according to claim 1, wherein creating the new trial variables further comprises applying a random mutation to a predetermined percentage of the chromosomes.

13. A system comprising:
a hardware processor, a computer readable memory, and a computer readable storage medium associated with a computing device;
program instructions to assign each of a plurality of entities to one of a plurality of treatment groups, wherein the plurality of entities are participants in a clinical trial; and
program instructions to, for each of the plurality of treatment groups:
for each of the entities in a group of the plurality of treatment groups, determine environmental features of an entity in real time during the clinical trial utilizing a deep learning environmental model outputting classified aspects of the entity's environment;
for each of the entities in the group of the plurality of treatment groups, obtain physiological measurements of the entity directly from a monitoring device of the entity during the clinical trial;
for each of the entities in the group of the plurality of treatment groups, determine an indication of how the entity is feeling in response to an active signal applied to the entity by analyzing digital images of the entity using a convoluted neural network;
for each of the entities in the group of the plurality of treatment groups, determine variables associated with the clinical trial;
for each of the entities in the group of the plurality of treatment groups, encode determined information about the entity during the clinical trial including the classified aspects of the entity's environment, the physiological measurements of the entity, the indication of how the entity is feeling, and the determined variables associated with the clinical trial, into a computer data structure as chromosomes using a genetic algorithm;
for each of the entities in the group of the plurality of treatment groups, iteratively update the chromosomes based on new determined information about the entity obtained during the clinical trial;
automatically determine one or more outlier chromosomes of the chromosomes;
automatically remove one or more outlier entities in the group of the plurality of treatment groups based on the determined outlier chromosomes;
determine a ranking of each of the entities in the group of the plurality of treatment groups based on a magnitude of values of the chromosomes corresponding to each of entity in the group;

for each group in the plurality of treatment groups, cross over portions of the encoded information of pairs of entities occupying adjacent positions in the ranking that describe aspects of the clinical trial to create new trial variables regarding aspects of the clinical trial, including dosage amounts of a medication; and measure fitness of each of the entities in the group of the plurality of treatment groups based on their respective chromosomes, wherein the program instructions are stored on the computer readable storage medium for execution by the hardware processor via the computer readable memory.

14. The system according to claim 13, further comprising program instructions to, for each of the plurality of treatment groups, agglomerate the entities in the group based on a determined level of similarity.

15. The system according to claim 14, further comprising program instructions to, for each of the plurality of treatment groups, apply density estimators to the entities in the group.

16. The system according to claim 15, further comprising program instructions to, for each of the plurality of treatment groups, identify the outlier chromosomes by applying a gaussian mixture model to all of the chromosomes in the group.

17. The system according to claim 16, wherein the removing the one or more outlier entities out of the group comprises moving the one or more outlier entities to another group of the plurality of treatment groups.

18. The system according to claim 16, wherein the removing the one or more outlier entities out of the group comprises moving the one or more outlier entities to a newly created group.

19. The system according to claim 13, wherein the encoded information includes information on the therapy in the clinical trial.

20. The system according to claim 13, wherein creating the new trial variables further comprises applying a random mutation to a predetermined percentage of the chromosomes.

* * * * *